United States Patent [19]
Piotrowski et al.

[11] Patent Number: 4,788,367
[45] Date of Patent: Nov. 29, 1988

[54] SYNTHESIS OF OLEFINS FROM KETONES USING BIS(ALKYLCHLOROALUMINO)METHANE

[75] Inventors: Andrzej M. Piotrowski, Houston; Dennis B. Malpass, La Porte, both of Tex.

[73] Assignee: Texas Alkyls Inc., Deer Park, Tex.

[21] Appl. No.: 116,846

[22] Filed: Nov. 5, 1987

[51] Int. Cl.$^4$ ................................................ C07C 1/20
[52] U.S. Cl. .................................... 585/357; 585/469; 585/638; 549/356
[58] Field of Search ........................ 585/638, 357, 469

[56] References Cited
PUBLICATIONS

J. of Organometallic Chem., 72(1974) C4–C4.
J. of Organometallic Chem., 225(1982) 71–85.

*Primary Examiner*—Curtis R. Davis
*Attorney, Agent, or Firm*—Richard P. Fennelly; Louis A. Morris

[57] ABSTRACT

Ketones are methylenated to form the corresponding olefin by reaction with a bis(alkylchloroalumino)methane, e.g., in the form of its dietherate.

11 Claims, No Drawings

SYNTHESIS OF OLEFINS FROM KETONES USING BIS(ALKYLCHLOROALUMINO)METHANE

BACKGROUND OF THE INVENTION

1. Field of the Invention

The present invention relates to the synthesis of olefins from ketones using bis(alkylchloroalumino) methane as an organoaluminum methylenating agent whereby the carbonyl oxygen atom of the ketone is replaced with a methylene group to form the corresponding olefin.

2. Description of the Prior Art

Conversion of a carbonyl function to a carbon-carbon double bond is a known industrial procedure. It is commonly achieved by use of phosphorus ylids in the Wittig reaction. Although such a reaction is general for both aldehydes and ketones, in certain instances poor yields of olefinic products are obtained when carbonyl compounds are attacked by the highly reactive bases used to generate phosphorus Ylids. In view of the market potential for the reaction and certain disadvantages in regard to use of Wittig reagents, some other alternatives have been examined.

Gem-dimetallic derivatives, such as bis-halomagnesiomethane, have been proposed for use (F. Bertini et al., Tetrahedron 26, 1281, 1970) but such geminal dimagnesium compounds are difficult to make and are thus expensive.

Geminal dialuminum compounds, such as bisdibromoaluminomethane, are more inexpensive to prepare but were found by A. Bongini et al. (J. of Organomet. Chem., 72 (1974) C4–C6) to be quite unreactive towards ketones.

Ashby et al. (J. of Organomet. Chem., 225 (1982) 71–85) utilized bis(diethylalumino) methane to ethylate 4-t-butylcyclohexanone. Ashby et al. observed 4-t-butyl-1-methylenecyclohexane in the product, but the relatively low yield (43%) would not justify use of bis(diethylalumino)methane as a Wittig reagent replacement.

SUMMARY OF THE INVENTION

The present invention relates to the use of bis(alyl-chloroalumino)methane reagents to convert ketones to olefins. Good yields (e.g., 50–90%) of ketones into olefins was achieved by using compounds containing mixed alkylchloroaluminum substitution (e.g., bis(chloromethylalumino)- and bis(chloroethylalumino)methane).

DETAILED DESCRIPTION OF THE INVENTION

The bis(alkylchloroalumino)methane reagents intended for use in accordance with the present invention have the formula:

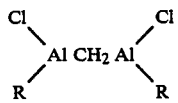

where R is a hydrocarbyl group, such as alkyl (e.g., $C_1$–$C_4$ alkyl, such as methyl or ethyl). Representative compounds include bis(chloromethylalumino)methane and bis(chloroethylalumino)methane. These reagents can be readily prepared by a redistribution reaction of bis(dichloroalumino)methane with trialkylaluminum (e.g., trimethylaluminum) or alkylmagnesium bromide (e.g., methylmagnesium bromide). This redistribution reaction can be conducted in a hydrocarbon or methylene chloride solvent in the presence of diethyl ether or tetrahydrofuran so that the dietherate can be formed. The use of these etherates is important, particularly when enolizable ketones (e.g., 4-phenylcyclohexanone) are to be reacted in order to prevent aldol condensation from occurring.

The types of ketones which can be reacted in accordance with the present invention can be varied quite widely. For example, cycloalkyl ketones, such as cyclohexanone and its derivatives (e.g., 4-t-butylcyclohexanone, 4-phenylcyclohexanone, and dihydrocarvone) can be used. Multi-ring (e.g., naphthalenic derived ketones such as alpha-tetralone and 4-chromanone can be treated by this process. Sterically hindered aliphatic ketones (e.g., diisopropyl ketone) also can be treated by the instant process. Aromatic ketones (e.g., benzophenone) can also be used. Molar ratios of ether to bis(alkylchloroalumino)methane can range from about 1:1 to about 100:1, with a preferred ratio being about 2:1. The preferred molar ratio of methylenating reagent to ketone is from about 1.1:1 to about 2:1.

The following Examples further illustrate the present invention.

COMPARATIVE EXAMPLE 1

Bis(dibromoalumino)methane in tetrahydrofuran (THF) was rfluxed with 1 molar equivalent of $Ph_2CO$ for 2 hours as described in J. Organometal. Chem., Vol. 72, C4–C6 (1974). No. 1,1-diphenylethylene ($Ph_2C=CH_2$) was formed.

EXAMPLE 1

Bis-dichloroaluminomethane (BDAM) (1.56 grams) was suspended in 50 milliliters of toluene and 1.2 milliliters of dry THF were added. After a homogeneous solution was formed, 1.36 grams of $Ph_2CO$ were added and the mixture was refluxed for 16 hours. The reaction mixture was poured into an ice/ether mixture. After the usual work up, 1.10 grams of $ph_2C:CH_2$ were isolated (82% yield).

EXAMPLE 2

BDAM (3.00 grams) was suspended in 40 milliliters of methylene chloride and 2 molar equivalents of THF were added at 0° C. After a homogeneous solution was formed, 1 molar equivalent of TEAL in 10 milliliters of hexane was added followed by 2.20 grams of 4-tert-butylcyclohexanone. After overnight stirring, reaction mixture was hydrolyzed and worked up as described in Example 1. A total of 1.50 grams of 4-tert-butyl-1-methylenecyclohexane was isolated (70% yield).

These results are more favorable than the 43% yield reported by Ashby et al. in J. Organometal. Chem., Vol. 225, 71–85 (1982).

COMPARATIVE EXAMPLE 3

BDAM (2.83 grams) was suspended in 40 milliliters of toluene and 2.2 milliliters of THF were added dropwise. After 10 minutes of stirring, 2.10 grams of 4-phenylcyclohexanone were added. The reaction mixture was refluxed for 1 hour and hydrolyzed with hydrated $Ca(OH)_2$ in the presence of $Et_3N$. After the usual work up, 0.21 grams of 4-phenyl-1-methylenecyclohexane was isolated (10% yield).

EXAMPLE 3

BDAM (3.00 grams) was suspended in 40 milliliters of toluene and 2 molar equivalents of THF were added at 0° C. After a homogeneous solution was formed, 1 molar equivalent (2 milliliters) of TEAL was added. After 10 minutes of stirring, 2.50 grams of 4-phenylcyclohexanone were added. After 3 hours of stirring the reaction mixture was hydrolyzed and worked up as described in Example 1. A total of 1.93 grams of 4-phenyl-1-methylenecyclohexane was isolated (78% yield).

EXAMPLE 4

BDAM (3.00 grams) was suspended in 30 milliliters of dry $CH_2Cl_2$. Two molar equivalents of ether were added dropwise to the chilled suspension. After about 10 minutes of stirring, a homogeneous solution was formed. At this point, 1 molar equivalent of TMAL (1.1 milliliter) was added. The reaction mixture was stirred at room temperature for 15 minutes and 2.00 grams of 4-phenylcyclohexanone were added. Vigorous reflux which quickly subsided was noticed. The reaction mixture was stirred at room temperature for 3 hours and hydrolyzed as described in Example 1. The aqueous layer was acidified to help separate the organic layer. After the usual work up and column separation 1.75 grams of 4-phenyl-1-methylenecyclohexane were isolated (88% yield).

EXAMPLE 5

BDAM (2.60 grams) was combined with ether (2 milliliters) and TMAL (1.0 milliliter) as described in Example 4, after which 1.50 grams of (+) dihydrocarvone were added. As in Example 4, a noticeably exotherm was observed. After 3 hours of stirring at room temperature, the reaction mixture was hydrolyzed as in Example 1. After the usual work up and column separation, 1.40 grams of 4-methyl-3-methylene-1-isopropenyl cyclohexane were isolated (95% yield).

EXAMPLE 6

BDAM (2.60 grams) was combined with ether (2 milliliters) and TMAL (1.0 milliliter) as described in Example 4. Then, 1.40 grams of 4-chromanone were added. After ½ hour of stirring, the reaction mixture was quenched with polyvinylpyridine and 0.1 molar sodium hydroxide solution (1 milliliter) at 0° C. The organic layer was separated from the polymer and the polymer was washed 5 times with 100 milliliters of ether. The organic layer and ether extracts were combined, washed with 0.1 molar solution of NaOH and dried over $MgSO_4$. The solvent was evaporated and 0.85 gram of 2,3-dihydro-4-methylenebenzopyran was separated on a short basic alumina column (61% yield).

EXAMPLE 7

BDAM (5.2 grams) was suspended in 80 milliliters of $CH_2Cl_2$. The suspension was chilled to 10° C. and 4 milliliters of ether were added. After ½ hour of stirring at room temperature, a homogeneous solution of BDAM etherate was chilled to 10° C. and 13.20 milliliters of a 3 molar solution of $CH_3MgBr$ in ether were slowly added. After 1 hour of stirring at room temperature, solids were removed by filtration and washed with three 100-milliliter portions of $CH_2Cl_2$. Some of the solvent was then evaporated to leave 53.0 grams of concentrated solution of methylenating reagent containing 2.36 weight percent Al and 3.60 weight percent Cl. Twenty grams of this solution were reacted with 1.50 grams of 4-phenylcyclohexanone. After hydrolysis and the usual work up, 1.26 grams (85% yield) of 4-phenyl-1-methylenecyclohexane was isolated.

The foregoing illustrate certain preferred embodiments of the present invention but should not be construed in a limiting sense. The scope of protection which is sought is given in the claims which follow.

We claim:

1. A process for the methenylation of the carbonyl oxygen atom of a ketone which comprises reacting the ketone with a bis(alkylchloroaluino)methane to form the corresponding olefin.

2. A process as claimed in claim 1 wherein the bis(alkylchloroalumino)methane has the formula:

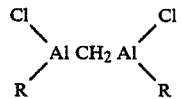

where R is hydrocarbyl.

3. A process as claimed in claim 2 where R is $C_1-C_4$ alkyl.

4. A process as claimed in claim 1 wherein the ketone is a cycloalkyl ketone.

5. A process as claimed in claim 1 wherein the ketone is a multi-ring naphthalenic derivative.

6. A process as claimed in claim 1 wherein the ketone is an aliphatic ketone.

7. A process as claimed in claim 1 wherein the ketone is an aromatic ketone.

8. A process as claimed in claim 1 wherein the molar ratio of bis(alkylchloroalumino)methane to ketone ranges from about 1.1:1 to about 2:1.

9. A process as claimed in claim 8 wherein the bis(alkylchloroalumino)methane has the formula:

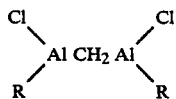

with R being $C_1-C_4$ alkyl.

10. A process for the methenylation of the carbonyl oxygen atom of a ketone which comprises reacting the ketone with the dietherate of a bis(alkylchloroalumino)methane, in a molar ration of dietherate to ketone of from about 1.1:1 to about 2:1, to form the corresponding olefin.

11. A process as claimed in claim 10 wherein the dietherate is formed using a molar ratio of ether to bis(alkylchloroalumino)methane which ranges from about 1:1 to about 100:1.

* * * * *